US012268793B2

(12) United States Patent
Fang et al.

(10) Patent No.: US 12,268,793 B2
(45) Date of Patent: Apr. 8, 2025

(54) LIQUID-CHEMICAL STERILIZATION SYSTEM WITH BIOLOGICAL INDICATOR

(71) Applicant: ASP Global Manufacturing GMBH, Schaffhausen (CH)

(72) Inventors: Yan Fang, Irvine, CA (US); Prabhakaran Jayabalan, Lake Forest, CA (US); Benjamin M. Fryer, Lake Forest, CA (US)

(73) Assignee: ASP Global Manufacturing GmbH (CH)

( * ) Notice: Subject to any disclaimer, the term of this patent is extended or adjusted under 35 U.S.C. 154(b) by 0 days.

(21) Appl. No.: 18/379,843

(22) Filed: Oct. 13, 2023

(65) Prior Publication Data

US 2024/0033385 A1 Feb. 1, 2024

Related U.S. Application Data

(62) Division of application No. 16/717,735, filed on Dec. 17, 2019, now Pat. No. 11,850,320.

(Continued)

(51) Int. Cl.
*A61L 2/18* (2006.01)
*A61L 2/28* (2006.01)
(Continued)

(52) U.S. Cl.
CPC .............. *A61L 2/18* (2013.01); *A61L 2/186* (2013.01); *A61L 2/28* (2013.01); *C12M 1/34* (2013.01);
(Continued)

(58) Field of Classification Search
CPC .......... A61L 2/0088; A61L 2/18; A61L 2/186; A61L 2/28; A61L 2202/12;
(Continued)

(56) References Cited

U.S. PATENT DOCUMENTS

| | | | |
|---|---|---|---|
| 4,743,537 A | 5/1988 | McCormick et al. | |
| 5,073,488 A | 12/1991 | Matner et al. | |

(Continued)

FOREIGN PATENT DOCUMENTS

| | | | |
|---|---|---|---|
| CN | 101061232 A | 10/2007 | |
| CN | 101611132 A | 12/2009 | |

(Continued)

OTHER PUBLICATIONS

Wiggins et al., "Sterrad Velocity Biological Indicator and Reader"; Division of Anaesthesiology, General Hospital, Respiratory, Infection Control, and Dental Devices; Office of Device Evaluation Center for Devices and Radiological Health; pp. 1-7.

(Continued)

*Primary Examiner* — Jennifer Wecker
*Assistant Examiner* — Brady C Pilsbury
(74) *Attorney, Agent, or Firm* — Lerner David LLP

(57) ABSTRACT

A sterilization system includes a vial, a carrier of microorganisms disposed in the vial, and a fluid management system having an output connectable to the vial for delivering a liquid chemical sterilant and a neutralizer thereto. Additionally, a growth medium may be delivered to the vial such that the vial and growth medium may assessed for a change to a visual characteristic indicative of sterilization inefficacy.

20 Claims, 3 Drawing Sheets

Related U.S. Application Data

(60) Provisional application No. 62/782,949, filed on Dec. 20, 2018, provisional application No. 62/782,931, filed on Dec. 20, 2018.

(51) Int. Cl.
*C12M 1/00* (2006.01)
*C12M 1/12* (2006.01)
*C12M 1/32* (2006.01)
*C12M 1/34* (2006.01)
*C12M 3/00* (2006.01)
*C12Q 1/22* (2006.01)

(52) U.S. Cl.
CPC ............ *C12M 23/12* (2013.01); *C12M 23/34* (2013.01); *C12M 23/38* (2013.01); *C12M 23/40* (2013.01); *C12M 23/48* (2013.01); *C12M 37/06* (2013.01); *C12Q 1/22* (2013.01); *A61L 2202/24* (2013.01)

(58) Field of Classification Search
CPC .. A61L 2202/15; A61L 2102/36; C12M 1/34; C12M 23/12; C12M 23/34; C12M 23/38; C12M 23/40; C12M 23/48; C12M 37/06; C12Q 1/22; A01N 25/02; A01N 37/16; A01P 1/00; A01P 3/00
See application file for complete search history.

(56) References Cited

U.S. PATENT DOCUMENTS

| | | | |
|---|---|---|---|
| 5,223,401 A | 6/1993 | Foltz et al. | |
| 5,418,167 A | 5/1995 | Matner et al. | |
| 5,834,313 A | 11/1998 | Lin | |
| 5,921,256 A | 7/1999 | Barin | |
| 6,025,189 A | 2/2000 | Bolea et al. | |
| 6,528,277 B1 | 3/2003 | Hendricks et al. | |
| 6,749,807 B1 | 6/2004 | Schindly et al. | |
| 9,322,046 B2 | 4/2016 | Chandrapati et al. | |
| 10,058,482 B2 | 8/2018 | Haindl et al. | |
| 10,444,050 B2 | 10/2019 | Zhang et al. | |
| 2003/0087441 A1 | 5/2003 | Lemus et al. | |
| 2003/0190256 A1 | 10/2003 | Halstead et al. | |
| 2008/0070272 A1 | 3/2008 | Franciskovich et al. | |
| 2008/0176318 A1 | 7/2008 | Wilson et al. | |
| 2009/0111173 A1 | 4/2009 | Sharpin | |
| 2010/0248215 A1 | 9/2010 | Halverson et al. | |
| 2010/0255526 A1 | 10/2010 | Braet et al. | |
| 2011/0064606 A1 | 3/2011 | Foltz et al. | |
| 2011/0182770 A1 | 7/2011 | Chandrapati et al. | |
| 2011/0217203 A1 | 9/2011 | Robole et al. | |
| 2012/0118338 A1 | 5/2012 | Nakanishi | |
| 2012/0186201 A1 | 7/2012 | Clouser et al. | |
| 2013/0273594 A1 | 10/2013 | Ahimou et al. | |
| 2014/0273072 A1 | 9/2014 | Franciskovich et al. | |
| 2016/0025607 A1 | 1/2016 | Sitton et al. | |
| 2017/0246330 A1 | 8/2017 | Lyon | |
| 2017/0253845 A1 | 9/2017 | Amin | |
| 2018/0065315 A1 | 3/2018 | Stein et al. | |
| 2018/0071418 A1 | 3/2018 | Bommarito | |
| 2018/0071421 A1 | 3/2018 | Fang et al. | |
| 2018/0187142 A1 | 7/2018 | Truong | |
| 2018/0245122 A1 | 8/2018 | Soto et al. | |
| 2019/0343975 A1 | 11/2019 | Biron | |
| 2020/0205414 A1* | 7/2020 | Limaye ................ A01K 45/007 |

FOREIGN PATENT DOCUMENTS

| | | |
|---|---|---|
| CN | 201581080 U | 9/2010 |
| CN | 107137741 A | 9/2017 |
| EP | 1025258 B1 | 6/2005 |
| EP | 3366315 A1 | 8/2018 |
| FR | 3058733 A1 | 5/2018 |
| JP | 2002-544504 A | 12/2002 |
| JP | 2010-504101 A | 2/2010 |
| JP | 2014-502503 A | 2/2014 |
| TW | 200912300 A | 3/2009 |
| WO | 0069475 A1 | 11/2000 |
| WO | 2005000364 A2 | 1/2005 |
| WO | 2012088048 A1 | 6/2012 |
| WO | 2015177821 A1 | 11/2015 |
| WO | 2017/184444 A1 | 10/2017 |
| WO | 2018025207 A1 | 2/2018 |

OTHER PUBLICATIONS

Australian Search Report for 2019407179 dated Sep. 9, 2024, 2 pages.

Chinese Search Report from 201980084373.2, dated Sep. 10, 2024, pp. 1-3.

PCT Notification of Transmittal of the International Search Report and the Written Opinion of the International Searching Authority, or the Declaration, International Application No. PCT/IB2019/061134, Date of Mailing Mar. 27, 2020, 13 Pages.

PCT Notification of Transmittal of the International Search Report and the Written Opinion of the International Searching Authority, or the Declaration; International Application No. PCT/IB2019/061194; Jun. 24, 2020; 18 Pages.

Search Report dated Feb. 5, 2024 from Office Action for Chinese Action No. 201980084373.2 issued Feb. 7, 2024. 4 pgs.

Bond WW. The author replies. Infection Control & Hospital Epidemiology. Oct. 1993;14(10):565-565. doi:10.1017/S0899823X00092291.

Sun Lei, et al., "Effect Monitoring of Ethylene Oxide Sterilization Technology", Emergency Public Health Emergency Management Office, Heilongjiang Center for Disease Control and Prevention, Harbin Heilongjiang 150030, China, Jul. 2016. 2 pgs.

* cited by examiner

LIQUID-CHEMICAL STERILIZATION SYSTEM WITH BIOLOGICAL INDICATOR

CROSS-REFERENCE TO RELATED APPLICATIONS

This application is a divisional of U.S. application Ser. No. 16/717,735, filed on Dec. 17, 2019, which claims the benefit of the filing date of U.S. Provisional Patent Application No. 62/782,931, filed Dec. 20, 2018, and of U.S. Provisional Patent Application No. 62/782,949, also filed Dec. 20, 2018, the disclosures of which are all hereby incorporated herein by reference.

FIELD

The subject matter disclosed herein concerns apparatuses and techniques for assessing the adequacy of a liquid chemical sterilization routine, particularly as applied to endoscope sterilization.

BACKGROUND OF THE INVENTION

Medical devices are typically sterilized before use to minimize the likelihood that a contaminated device might be used on a subject, which could cause an infection in the subject. Various sterilization techniques may be employed, such as steam, hydrogen peroxide, and vapor phase sterilization, either with or without a gas plasma and ethylene oxide (EtO).

Certain sterilization techniques are conducted at pressures other than ambient pressure or atmospheric pressure. For example, the STERRAD® System, STERRAD® NX System or STERRAD® 100NX System of Advanced Sterilization Products, Division of Ethicon US, LLC, a Johnson & Johnson company, are examples of sterilization systems, or sterilizers, that vaporize hydrogen peroxide and operate at low pressures, e.g., less than 200 millitorr.

Various elongate medical devices having lumens, e.g., endoscopes, are challenging to sterilize by a vapor sterilant, e.g., vaporized hydrogen peroxide, for various reasons. For example, because pressure in a lumen decreases from the lumen's inlet as a function of length and diameter, the pressure drop must be overcome to ensure that sterilant passes through the entire lumen and reaches all surfaces of the lumen. Further, lumens may collect debris or be blocked by fluids, such as rinse water.

Often vapor-based sterilization routines incorporate a sterilization indicator, such as a biological indicator or a chemical indicator, which may provide an indication of the effectiveness of a sterilization cycle. Even though such indicators may be positioned close to an endoscope in a sterilization chamber, they may not be reliable for assessing the sterility of the endoscope because the portions of the endoscope that are most difficult to sterilize are typically deep within the endoscope's lumens.

SUMMARY OF THE INVENTION

Disclosed herein is a sterilization system comprising a vial, a carrier disposed in the vial, and a fluid management system. The fluid management system includes an output connectable to the vial for delivery of liquids thereto. Such liquids include at least a liquid-chemical sterilant (e.g., peracetic acid) and a neutralizer (e.g., sodium metabisulfite). Accordingly, the fluid management system may include a source of a liquid-chemical sterilant and a source of a neutralizer. The sterilization system may further include a fixture that includes a first segment having a needle that is connected to the output of the fluid management system and a second segment having a cavity containing the vial. The first segment and second segment may be connected by a hinge such that a rotation of the first segment about the hinge causes the needle to penetrate the vial. The vial may include a cover that may also be pierced by the needle. A medical device having a lumen (e.g., an endoscope) may be connected between the needle and the output.

The carrier in the vial includes, e.g., spores or microorganisms disposed thereon or therein. For example, the carrier may comprise *Geobacillus stearothermophilus* spores. The sterilization system may include a growth medium (e.g., α-MUG) that may be used to encourage outgrowth of the spores or microorganisms. Thus, the fluid management system may include a source of a liquid growth medium. Alternatively or additionally, the growth medium may be provided in a second vial and disposed in the second cavity.

The sterilization system may be used to determine a sterility (or lack thereof) of a medical device that was or is being subject to a sterilization cycle in the sterilization system. The method may include steps of inserting the vial that contains the carrier of microorganisms into the cavity of the fixture, penetrating the needle into the vial, and introducing the liquid-chemical sterilant into the vial through the needle. Further, a lumen of a medical device, such as an endoscope, may be connected between the source of sterilant and the needle, such that the sterilant flows through the lumen before it is introduced to the vial. The vial may then be incubated while the liquid-chemical sterilant disposed therein at between approximately 30° C. and approximately 50° C., e.g., at 35° C. Following incubation, the liquid chemical sterilant may be withdrawn from the vial through the needle.

Next, the neutralizer may be introduced into the vial through the needle and subsequently withdrawn from the vial through the needle. Then, the growth medium may be introduced into the vial through the needle, either from the source of growth medium of the fluid management system, or from the second vial disposed in the second cavity of the fixture. The vial, i.e., the vial with the carrier and growth medium disposed therein, may then be incubated at between approximately 50° C. and approximately 60° C., e.g., at 57° C.

While the vial is being incubated, a visual characteristic of the growth medium may be monitored in order to determine a change to the visual characteristic. The visual characteristic may include a fluorescence intensity.

At any step of a sterilization cycle, but preferably at a first step or a final step, the system may sterilize at least some of its fluidic components, such tubes, valves, and pumps, by flowing the liquid-chemical sterilant through those components.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

DETAILED DESCRIPTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Automated sterilization equipment and routines for endoscopes that employ a liquid-chemical sterilant, e.g., hydrogen peroxide or peracetic acid, are being developed to overcome certain shortcomings associated with sterilizing endoscopes using vapor-chemical sterilants. However, as with the vapor-based processes, development of a reliable technique for assessing whether the endoscope has been sterilized remains a challenge. Moreover, the biological indicators that are used in vapor-based processes are not suitable for use in liquid-based processes because such indicators are designed to have gaseous sterilant, but not liquid sterilant, removed therefrom. Further, such indicators typically require a user to break an ampule containing a growth medium. When a liquid-chemical sterilant is used, there would thus remain a risk of burns to the user from residual liquid sterilant. Thus, it would be advantageous to provide a system capable of manipulating a biological indicator for use with a liquid-chemical sterilant that does not require user intervention. However, such a system should be designed to be sterilized to avoid build-up of contaminants therein. Proposed herein are devices and methods that may be used to determine whether an endoscope has been sterilized by a sterilization routine employing a liquid-chemical sterilant that further address these design requirements.

Figure 1:
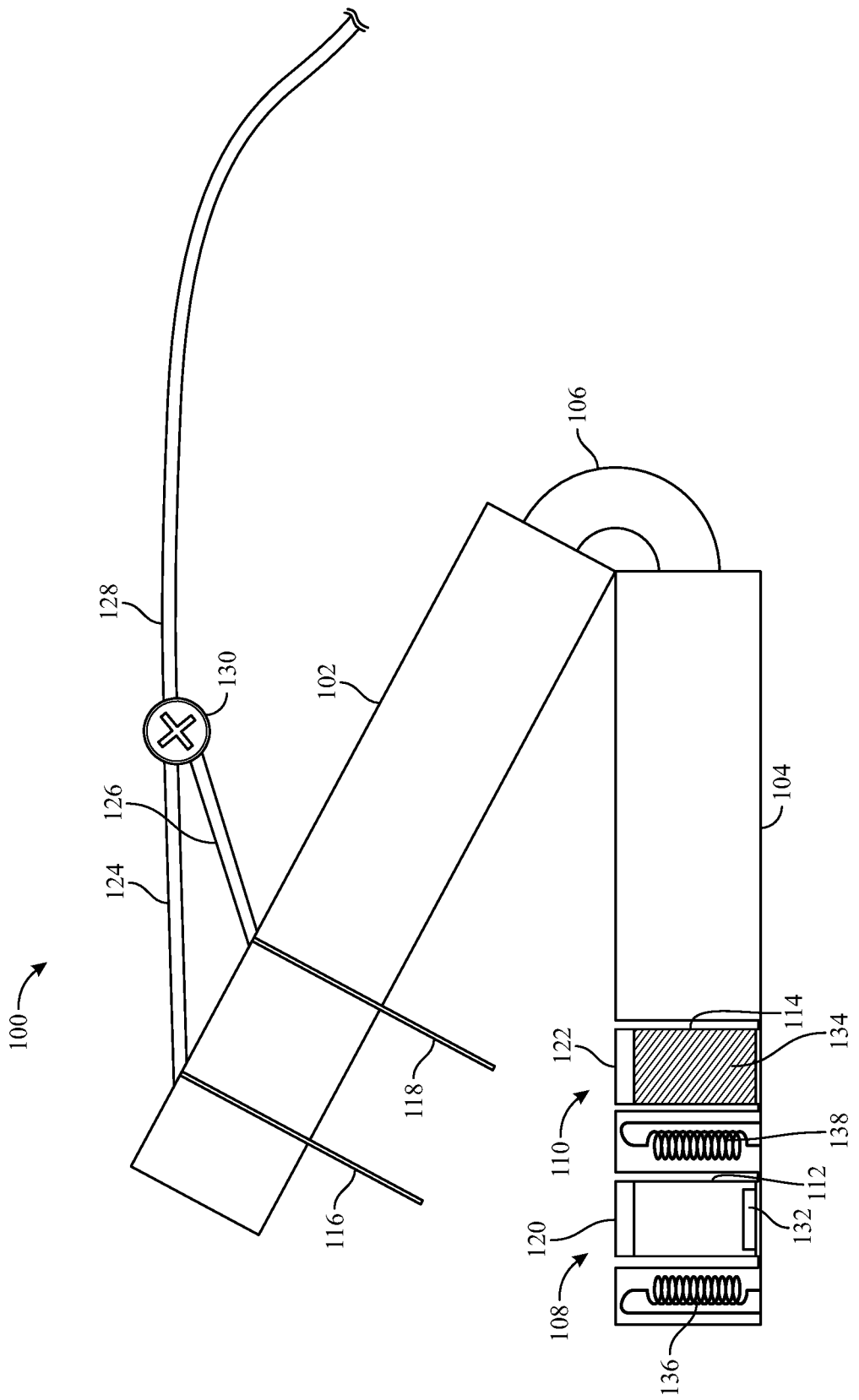
FIG. 1 depicts a schematic of a fixture in an open configuration for use with a liquid-chemical sterilization system to assist in assessments of sterilization efficacy.
Figure 2:
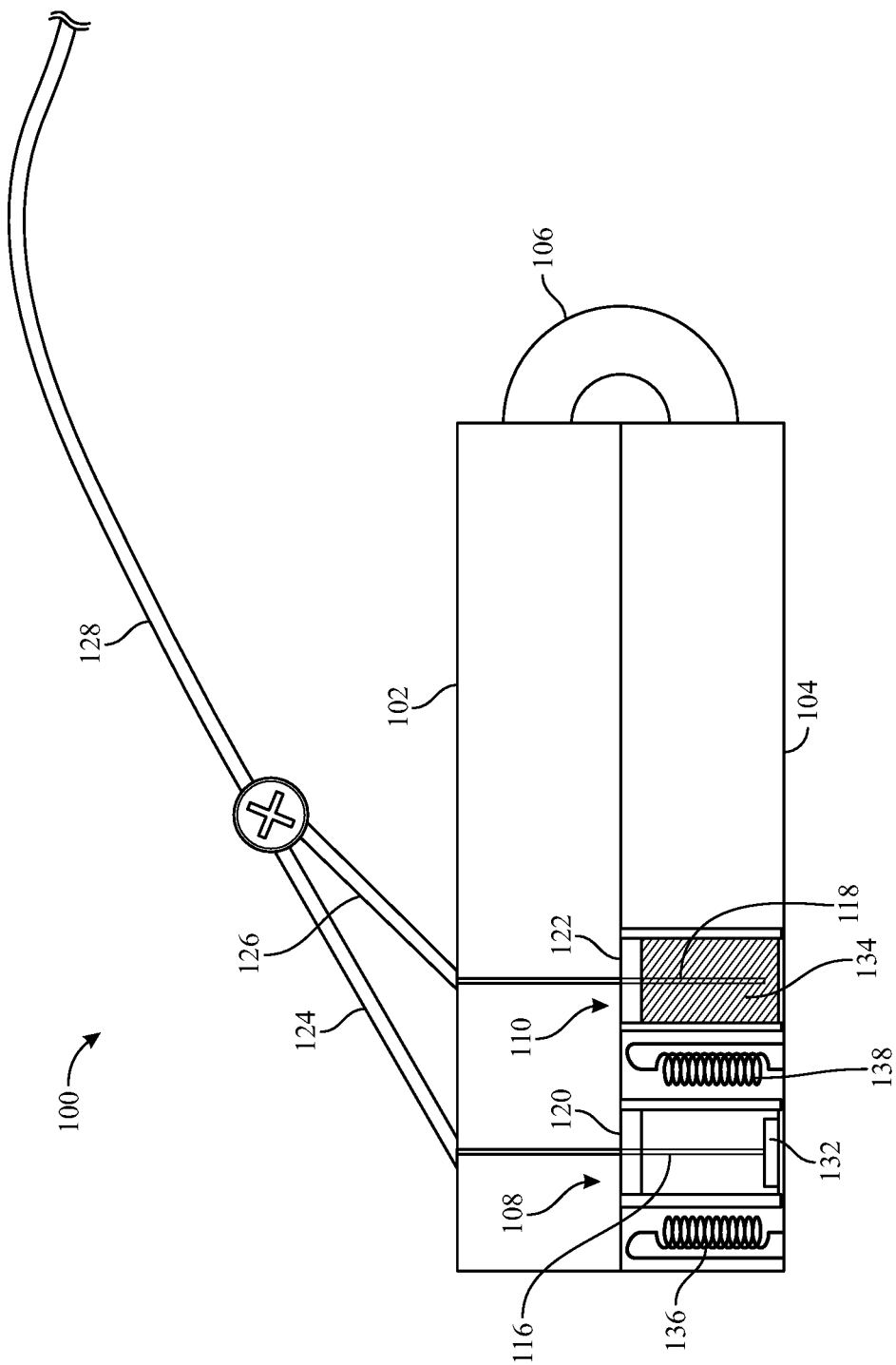
FIG. 2 depicts a schematic of the fixture of FIG. 1 in a closed configuration.

FIGS. 1 and 2 reflect a fixture 100 that may be used in conjunction with or form a portion of a liquid-chemical sterilization system. Fixture 100 may assist in assessments of medical devices, particularly endoscopes, subject to a sterilization routine by the system. FIG. 1 reflects fixture 100 in an open and unused configuration whereas FIG. 2 reflects fixture 100 in a closed configuration. Fixture 100 includes a first segment 102 joined to a second segment 104 by a hinge 106, e.g., a live hinge. A first cavity 108 and a second cavity 110 may be formed in second segment 104. Tubular passages may be formed in first segment 102 that are suitable for holding capillary tubes or hollow needles, e.g., first needle 116 and second needle 118. Further, heating elements, such as heating coils 136 and 138 may be disposed in second segment 104. Heating coils 136 and 138 are preferably disposed adjacent to cavity 108 such that they may be used to heat liquids disposed within cavity 108. Heating coils 136 and 138 may include contacts on the bottom for passing electricity therethrough. Although not shown, fixture 100 may further include componentry such as light sources and light detectors capable of assessing changes to a visual characteristic of a liquid, e.g., color changes or fluorescence intensity changes of a liquid in first cavity 108. Alternatively such componentry may be located adjacent to a location where cavity 108 may be disposed in the sterilization system.

First cavity 108 and second cavity 110 are suitable for holding liquids. Alternatively or additionally, they are suitable for maintaining positions of vials disposed therein. For example, as reflected in FIG. 1, a first vial 112 may be disposed in first cavity 108 and a second vial 114 may be disposed in second cavity 110. In those embodiments where liquid is disposed directly in one or both of the cavities, i.e., without a vial, the cavity may be sealed with a cover that may be breached to access the fluid. For example, a layer of foil, e.g., aluminum, may be used to cover cavity 108, cavity 110, or both. The layer of foil may be breached or pierced, e.g., by needles 116, 118, or both. In those embodiments incorporating first vial 112, second vial 114, or both, the vials may be individually covered to seal the vials. As reflected in FIGS. 1 and 2, first vial 112 includes a cover 120 and second vial 114 includes a cover 122. Accordingly, vials 112 and 114 may be provided as sterilized consumables that may be disposed in cavities 108 and 110 before commencing a sterilization routine and removed therefrom after the sterilization routine.

Vials 112 and 114 may further include features of a biological indicator. Specifically, disk or carrier 132 that contains or is impregnated with a source of microorganisms, e.g., spores, or active enzymes. Carrier 132 may be disposed in first vial 112. Spores from *Bacillus, Geobacillus,* and Clostridia species are often used to monitor sterilization processes using chemical sterilants. Accordingly, carrier 132 may be impregnated with spores from *Bacillus, Geobacillus,* and/or Clostridia species. For example, sterilization process resistant spores can include, but are not limited to, at least one of *Geobacillus stearothermophilus* spores, *Bacillus subtilis* spores, *Bacillus atrophaeus* spores, *Bacillus megaterium* spores, *Bacillus coagulans* spores, *Clostridium sporogenes* spores, *Bacillus pumilus* spores and combinations thereof.

Carrier 132 may be water-absorbent and may be formed of filter paper. Sheet-like materials such as cloth, nonwoven polypropylene, rayon or nylon, and microporous polymeric materials may also be used. Non-water absorbent materials are also appropriate for use, such as metals (e.g., aluminum or stainless steel), glass (e.g., glass beads or glass fibers), porcelain, or plastic. Additionally, carrier 110 can be constructed of a combination of the aforementioned materials. In some embodiments, carrier 110 may have a thickness of approximately 0.1 to 0.5 millimeters.

Further, a growth medium 134 may be disposed in second vial 114. The growth medium should be capable of promoting growth of any viable microorganisms or other source of biological activity disposed on carrier 132. Preferably, the microorganisms are chosen to generate enzymes that interact with enzyme substrates of the growth medium to create a change in a visual characteristic of the growth medium, e.g., by causing a color change or fluorescence intensity change to the growth medium. Continued growth of the microorganisms in the growth medium causes an increase in the concentration of the detectable product in the growth medium. In certain embodiments, the detectable product is a fluorophore. Thus, an increase in concentration of the detectable product causes an increase in fluorescence. That is to say, the detectable product is detectable via changes in fluorescence intensity.

Enzymes and enzyme substrates that may be used to detect efficacy of a sterilization cycle are identified in U.S. Pat. No. 5,073,488, entitled "Rapid Method for Determining Efficacy of a Sterilization Cycle and Rapid Read-Out Biological Indicator," issued Dec. 17, 1991, the disclosure of which is incorporated by reference herein; U.S. Pat. No. 5,418,167, entitled "Rapid Read-Out Biological Indicator," issued May 23, 1995, the disclosure of which is incorporated by reference herein; U.S. Pat. No. 5,223,401, entitled "Rapid Read-Out Sterility Indicator," issued Jun. 29, 1993, the disclosure of which is incorporated by reference herein; and U.S. Pat. No. 9,322,046, entitled "Biological Sterilization Indicator," issued Apr. 26, 2016, the disclosure of which is incorporated by reference herein.

Suitable enzymes may include hydrolytic enzymes and/or enzymes derived from spore-forming microorganisms, such as *Bacillus subtilis*. Enzymes from spore-forming microorganisms that can be useful in exemplary biological indicators may include beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, tyrosine aminopeptidase, phenylalanine aminopeptidase, beta-D-glucuronidase, alpha-L-arabinofuranosidase, N-acetyl-beta-glucosaminodase, beta-D-cellobiosidase, alanine aminopeptidase, proline aminopeptidase, fatty acid esterases and combinations thereof.

In some exemplary methods for determining efficacy of a sterilization cycle as disclosed herein, enzyme substrates are converted to detectable product. For instance, an enzyme substrate may be characterized by a first emission spectrum (e.g., a first fluorescent emission spectrum) and a detectable product may be characterized by a second emission spectrum (e.g., a second fluorescent emission spectrum).

In some exemplary methods for determining efficacy of a sterilization cycle as disclosed herein, suitable enzyme substrates of use may include fluorogenic enzyme substrates. Useful fluorogenic enzyme substrates may be selected from: fluorogenic 4-methylumbelliferyl derivatives (hydrolysable to 4-methylumbelliferone ("4-Mu"), derivatives of 7-amido-4-methyl-coumarin, diacetylfluorescein derivatives, fluorescamine and combinations thereof.

Exemplary 4-methylumbelliferyl derivatives may be selected from: 4-methylumbelliferyl-2-acetamido-4, 6-β-benzylidene-2-deoxy-β-D-glucopyranoside, 4-methylumbelliferyl acetate, 4-methylumbelliferyl-N-acetyl-β-D-galactosaminide, 4-methylumbelliferyl-N-acetyl-α-D-glucosaminide, 4-methylumbelliferyl-N-acetyl-β-D-glucosaminide, 2'-(4-methylumbelliferyl)-α-D-N-acetyl neuraminic acid, 4-methylumbelliferyl α-L-arabinofuranoside, 4-methylumbelliferyl α-L-arabinoside, 4-methylumbelliferyl butyrate, 4-methylumbelliferyl 13-D-cellobioside, methylumbelliferyl β-D-N,N' diacetyl chitobioside, 4-methylumbelliferyl elaidate, 4-methylumbelliferyl β-D-fucoside, 4-methylumbelliferyl α-L-fucoside, 4-methylumbelliferyl β-L-fucoside, 4-methylumbelliferyl α-D-galactoside, 4-methylumbelliferyl β-D-galactoside, 4-methylumbelliferyl α-D-glucoside, 4-methylumbelliferyl β-D-glucoside, 4-methylumbelliferyl (3-D-glucuronide, 4-methylumbelliferyl p-guanidinobenzoate, 4-methylumbelliferyl heptanoate, 4-methylumbelliferyl α-D-mannopyranoside, 4-methylumbelliferyl β-D-mannopyranoside, 4-methylumbelliferyl oleate, 4-methylumbelliferyl palmitate, 4-methylumbelliferyl phosphate, 4-methylumbelliferyl propionate, 4-methylumbelliferyl stearate, 4-methylumbelliferyl sulfate, 4-methylumbelliferyl β-D-N,N',N"-triacetyl-chitotriose, 4-methylumbelliferyl 2,3,5-tri-o-benzoyl-α-L-arabinofuranoside, 4-methylumbelliferyl-p-trimethylammonium cinnamate chloride, 4-methylumbelliferyl β-D-xyloside and combinations thereof.

In certain embodiments, the fluorescent response may be based on the naturally occurring alpha-glucosidase enzyme found in the *Geobacillus stearothermophilus* spore coat, which contains the enzyme and which is believed to be important in the germination of G. *stearothermophilus*. Alpha-glucosidase may be used to hydrolyze the bond between the glucose and 4-methylumbelliferyl moieties of 4-methylumbelliferyl α-D-glucopyranoside (α-MUG). α-MUG is not fluorescent. However, following hydrolyzation and separation of the moieties, the 4-Methylumbelliferone (4-MU) product is fluorescent. 4-MU fluoresces when excited by an external energy source, such as a light source that emits light having a wavelength of between approximately 360 and 370 nanometers. So excited, 4-MU emits light having a wavelength of between approximately 440 and 460 nanometers. In certain embodiments, the light source emits light having a wavelength of approximately 365 nanometers and the 4-MU emits light having a wavelength of 450 nm. The fluorescence of 4-MU is pH dependent. For example, when excited by light having a wavelength of 365 nanometers, the intensity of the emitted light is highest at a pH of 10.3. The intensity decreases with pH until about a pH of 7. Below this pH the intensity becomes negligible.

Based on the foregoing, because carrier 132 and growth medium 134 are combined in vial 112, vial 112 may be considered a biological indicator.

Needles 116 and 118 are aligned, respectively, with cavities 108 and 110, such that upon transitioning fixture 100 from the open configuration of FIG. 1 to the closed configuration of FIG. 2, needles 116 and 118 puncture covers 120 and 122 to penetrate into vials 112 and 114, respectively, such that liquid can be introduced into or removed from vials 112 and 114. Needles 116 and 118 should be sufficiently long such that they can contact or nearly contact the bottom of the corresponding vial in the closed configuration to enable removal of all or substantially all of the liquid therefrom. When carrier 132 is disposed on the bottom of vial 112, needle 116 may contact or nearly contact its surface.

Fixture 100, i.e., at least first segment 102, second segment 104, and hinge 106, may be fabricated by any appropriate manufacturing method, e.g., injection molding, machining, or 3D printing. In those embodiments where some features, e.g., needles 116 and 118, and heating coils 136 and 138 are manufactured by a separate process, they may be assembled and secured into the fixture, e.g., by press-fit or using an adhesive, such as an epoxy.

Tubing may be connected to needles 116 and 118 to enable transfer of fluid from the cavities or vials. For example, a first tube 124 may be connected to needle 116 and a second tube 126 may be connected to needle 118. Tubes 124 and 126 may each be connected to a third tube 128 via a multi-directional valve 130. Tube 128 may connect to a fluid management system 200 of a liquid sterilization system such that the system may introduce and remove various liquids to and from vials 112 and 114.

Figure 3:
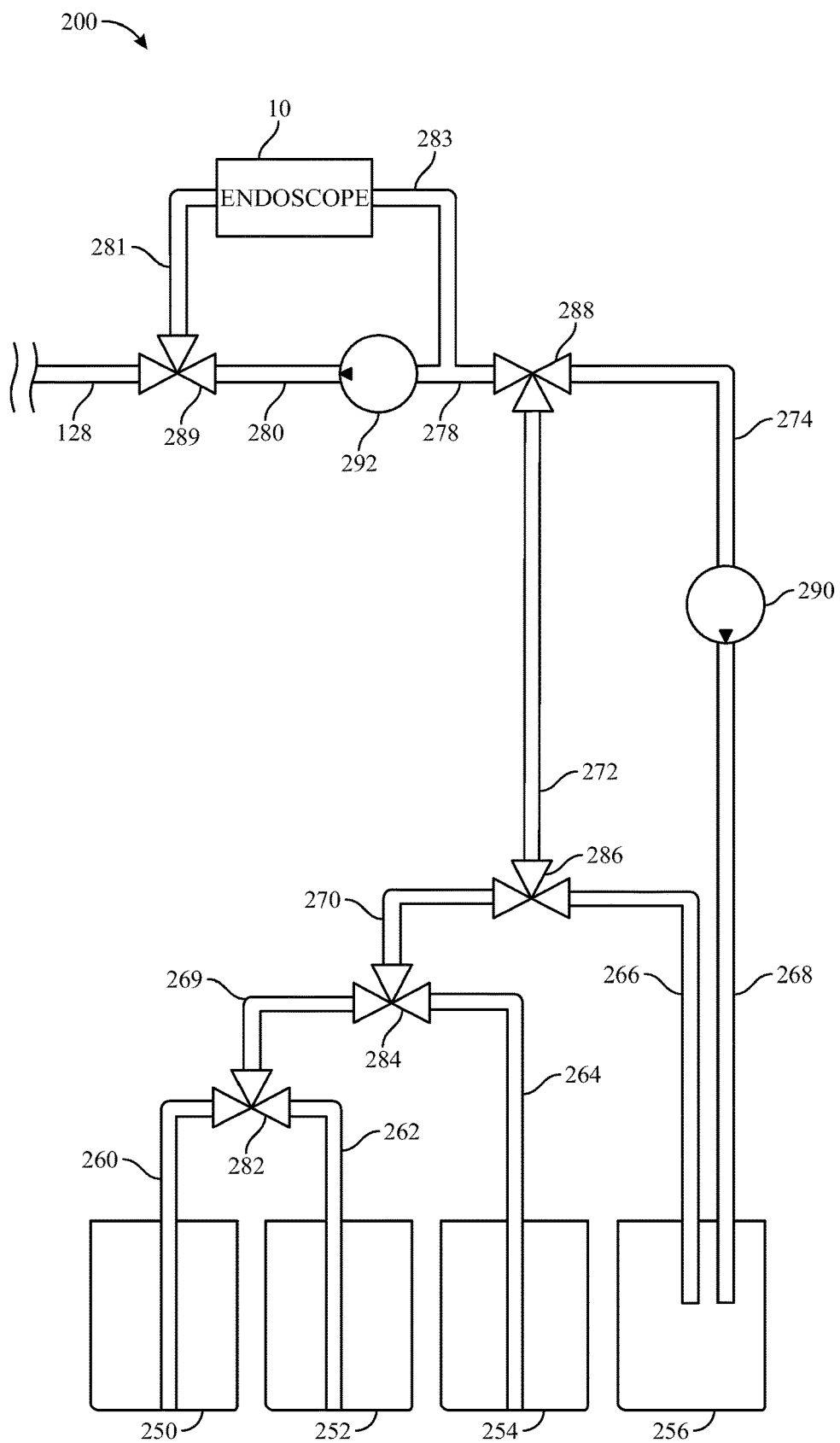
FIG. 3 depicts a block diagram of fluid management system for use with the fixture of FIGS. 1 and 2 and the liquid-chemical sterilization system.

A fluid management system 200 of a liquid sterilization system is shown in block form in FIG. 3. System 200 includes various sources of liquids, such as a source 250 of a liquid-chemical sterilant, e.g., peracetic acid or hydrogen peroxide, and a source 252 of a liquid reducing agent or neutralizer, e.g., sodium metabisulfite or sodium bisulfite, which may be used to neutralize the sterilant. Optionally, a source 254 of a growth medium may additionally be provided. In those embodiments that include source 254 of growth medium, system 200 may be used with a fixture 100 that lacks cavity 110, vial 114, and growth medium 134. System 200 may additionally include a drain 256.

Various tubes and valves connect sources 250 and 252 (and 254 when employed), as well as drain 256, to fixture 100 via tubes 124 and 128 (and 126 when source 254 is not employed). In some embodiments, an endoscope 10 may be disposed between system 200 and tube 128 such that liquids from any one of sources 250, 252, or 254 may first flow through lumens of the endoscope before entering vial 112. Typically, however, only sterilant from source 250 is flowed through endoscope 10, which may assist in the assessment of sterility made using vial 112 should provide a more accurate indication of the endoscope, including its lumens.

As seen in FIG. 3, system 200 includes tubes 260, 262, 264, 266, 268, 269, 270, 272, 274, 278, 280, 281, and 283. Either tube 280, valve 289, or the junction between valve 289 and tube 128 may be considered an output from system 200 and thus may be referred to herein as an output or outputs. System 200 also includes valves 282, 284, 286, 288, and 289, which may be three-way valves. System 200 also includes pumps 290 and 292. Thus, sterilant from source 250 may be propelled by pump 292 from source 250 to vial 112 via tube 260, valve 282, tube 269, valve 284, tube 270, valve 286, tube 272, valve 288, tube 278, tube 280, and then output from system 200 via valve 289, to tube 128, tube 124, and needle 116. Optionally the sterilant may be flowed through a recirculation line including tube 281, a lumen of a medical device (e.g., endoscope 10), tube 283, tube 278 tube 280 and valve 289 before a portion of the sterilant is output from system 200 via valve 289. Neutralizer from source 252 may be propelled by pump 292 from source 252 to vial 112 via tube 262, valve 282, tube 269, valve 284, tube 270, valve 286, tube 272, valve 288, tube 278, tube 280, and then output from system 200 via valve 289, to tube 128, tube 124, and needle 116.

Growth medium may be provided to vial 112 from either vial 114 or from source 254. With reference to FIG. 2, in those instances where growth medium 134 is supplied to vial 112 from vial 114, valve 130 is oriented such that tubes 128 and 126 are in fluid communication but not in fluid communication with tube 124. Growth medium 134 may be removed from vial 114 under pressures generated from pump 290 until growth medium 134 is contained in tube 128. Then, the orientation of valve 130 is changed such that tubes 128 and 124 are in fluid communication but not in fluid communication with tube 126. Growth medium 134 may then be advanced from tube 128 into vial 112 under pressures generated by pump 292. Where growth medium is provided from source 254, it may be propelled by pump 292 from source 254 to vial 112 via tube 264, valve 284, tube 270, valve 286, tube 272, valve 288, tube 278, tube 280, and then output from system 200 via valve 289, to tube 128, tube 124, and needle 116.

Draining or flushing the system may be achieved by opening the valves and operating pump 290 such that the liquids may flow into drain 256 via tubes 266 and 268. Drainage may assist in priming system 200, sterilizing system 200, or preparing system 200 for reuse.

The sterilization system may further include a processor, a non-transitory storage medium, and a user interface. The non-transitory storage medium may include computer-executable instructions or software capable of instructing the processor to activate the various pumps and orient the various valves such that fluid may be transferred through from sources 250, 252, and 254 (if included) and to vials 112 and 114 (if included) as described above. The processor may also be capable of receiving inputs from a light detector such that it may determine whether there has been any change to color or fluorescence of the growth medium and, based thereon, may abort the sterilization cycle or provide feedback to a user via the user interface.

By virtue of the embodiments illustrated and described herein, Applicant has devised a method and variations thereof for assessing the efficacy of a sterilization routine performed by an automated liquid-chemical sterilization system. The method and variations may include the following steps. First, a vial (e.g., 112) may be provided including a carrier of microorganisms (e.g., 132). The vial may be placed in a cavity to contain it and position it relative to a tube or needle (e.g., 116, 280) that may be inserted therein, which may include a step of piercing a barrier (e.g., 120) sealing the top of the vial. Further, the step of piercing the barrier may include closing a fixture (e.g., 100) to change the configuration of the fixture from an open configuration (e.g., FIG. 1) to a closed configuration (e.g., FIG. 2), which causes the needle to penetrate through the barrier to dispose it in the vial. Fixture 100 may be placed in a sterilization chamber of the sterilization system such that it and the outside of vial 112 may be subject to a sterilization routine alongside a medical device, e.g., an endoscope.

After the tube or needle is positioned in the vial, various steps of liquid transport may commence. First, a volume liquid chemical sterilant, e.g., peracetic acid or hydrogen peroxide, sufficient to fill the vial is introduced into the vial from a source of the liquid chemical sterilant, e.g., source 250. In certain variations, the liquid chemical sterilant may flow through at least one lumen of an endoscope before reaching vial 112. The vial and sterilant may then be heated, e.g., via heating elements 136 and 138, to between approximately 30° C. and approximately 60° C., which assists the sterilant to kill the microorganisms within the BI by increasing the inactivation kinetics between the sterilant and the microorganisms. When peracetic acid is used, inactivation kinetics may be maximized at approximately 35° C. Subsequently, the liquid chemical sterilant may be removed from the vial and drained from the system. Second, a volume of neutralizer, e.g., sodium metabisulfite or sodium bisulfite, sufficient to fill the vial is introduced into the vial from a source of the neutralizer, e.g., source 252. Then, that volume of neutralizer may be removed from the vial and drained from the system. In preferred variations, the peracetic acid and the neutralizer remain in the vial for approximately the same amount of time they are in contact with the endoscope. Third, the growth medium may be introduced into the vial. Two techniques for doing so have been detailed above.

With the growth medium in the vial, assessment of the efficacy of the sterilization cycle may begin. First, heating elements (e.g., 136 and 138) may be activated to incubate the vial and stimulate outgrowth of any spores that may have survived after removal of the sterilant. For example, incubation may maintain the temperature of the vial between approximately 50° C. and approximately 60° C., e.g., 57° C., for approximately thirty minutes. In those embodiments where fixture 100 includes light sources and detectors, the sterilization system may assess changes to a visual characteristic of the growth medium in the vial over the entire thirty minutes or a portion thereof to determine whether any spores may have survived and, based thereon, determine whether the sterilization cycle was efficacious. In those embodiments where fixture 100 does not include heating elements, light sources and detectors, or a combination thereof, the vial may be removed from fixture 100 and the sterilization system and placed into a well of a biological-indicator assessment device, such as the Reader of the commercially available STERRAD VELOCITY™ system, manufactured by applicant. The STERRAD VELOCITY™ Reader, ASP part no. 43220, may then incubate the vial and assess the growth medium therein for any color or fluorescence changes occurring determine whether the sterilization cycle was efficacious.

In further variations of the method, system 200 may flow the liquid-chemical sterilant through all of its components to sterilize itself. Additionally, system 200 may fill its components with one of the liquids to prime the system with that liquid before commencing the step of introducing a volume of that liquid to the vial Any of the examples or embodiments described herein may include various other features in addition to or in lieu of those described above. The teachings, expressions, embodiments, examples, etc., described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are in the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

The invention claimed is:

1. A method of determining a sterility of a medical device sterilized by a sterilization system, comprising:
   inserting a vial into a cavity, the vial containing a carrier of microorganisms;
   penetrating a needle into the vial;
   introducing a liquid-chemical sterilant into the vial through the needle;
   incubating the vial with the liquid-chemical sterilant disposed therein;
   withdrawing the liquid-chemical sterilant from the vial through the needle;
   introducing a neutralizer into the vial through the needle;
   withdrawing the neutralizer from the vial through the needle;
   introducing a growth medium into the vial through the needle; and
   incubating the vial with the growth medium disposed therein.

2. The method of claim 1, further comprising monitoring and determining a change of a visual characteristic of the growth medium.

3. The method of claim 2, wherein the visual characteristic comprises a fluorescence intensity.

4. The method of claim 2, further comprising passing a volume of the liquid-chemical sterilant through a lumen of the medical device before introducing the volume of the sterilant into the vial, wherein the medical device is an endoscope.

5. The method of claim 4, wherein the step of incubating the vial with the growth medium therein includes heating the vial to a temperature between approximately 50° C. and approximately 60° C.

6. The method of claim 5, wherein the step of incubating the vial with the liquid-chemical sterilant therein includes heating the vial to a temperature between approximately 30° C. and approximately 50° C.

7. The method of claim 6, wherein the sterilization system includes a plurality of fluid sources, tubes, valves, and pumps, the method further comprising sterilizing at least some of the fluid sources, tubes, valves, and pumps with the liquid-chemical sterilant.

8. The method of claim 6, wherein the liquid-chemical sterilant comprises peracetic acid or hydrogen peroxide.

9. The method of claim 1, wherein the step of penetrating the needle further includes moving the sterilization system from an open configuration to a closed configuration causing the needle to penetrate a barrier of the vial.

10. The method of claim 1, wherein the neutralizer comprises sodium metabisulfite or sodium bisulfite.

11. The method of claim 1, wherein the liquid-chemical sterilant remains in the vial for a first time duration, and the neutralizer remains in the vial for a second time duration, the first time duration being approximately equal to the second time duration.

12. The method of claim 11, wherein incubating the vial with the growth medium step is for a third time duration approximately equal to thirty minutes.

13. A method of determining a sterility of a medical device, comprising:
   inserting a vial into a cavity of a fixture, the vial containing a carrier of microorganisms;
   moving a first segment of the fixture with respect to a second segment of the fixture to penetrate the vial with a needle;
   introducing at least one fluid into the vial through the needle;
   incubating the vial with the at least one fluid disposed therein; and
   withdrawing at least one fluid from the vial through the needle.

14. The method of claim 13, wherein at least one fluid is a liquid-chemical sterilant or a growth medium.

15. The method of claim 14, further comprising the step of introducing a neutralizer into the vial through the needle.

16. The method of claim 13, wherein the introducing step is performed by a first pump fluidly connected by at least one valve and at least one tube to the vial, and the withdrawing step is performed by a second pump fluidly connected by at least one valve and at least one tube to the vial.

17. The method of claim 16, wherein a non-transitory storage medium instructs a processor to activate the first and second pumps and orient at least one valve such that at least one fluid is introduced to the vial or withdrawn from the vial.

18. The method of claim 13, wherein the fixture further includes a heating element adjacent to the vial, and the incubating step is performed by the heating element.

19. The method of claim 13, further comprising passing a volume of at least one fluid through a lumen of the medical device before introducing the volume of the at least one fluid into the vial, wherein the medical device is an endoscope.

20. A method of determining a sterility of a medical device, comprising:
   inserting a vial into a cavity of a fixture, the vial containing a carrier of microorganisms;
   moving a first segment of the fixture with respect to a second segment of the fixture to penetrate the vial with a needle;
   introducing a liquid-chemical sterilant into the vial through the needle;
   incubating the vial with the liquid-chemical sterilant disposed therein;
   withdrawing the liquid-chemical sterilant from the vial through the needle;
   introducing a neutralizer into the vial through the needle;
   withdrawing the neutralizer from the vial through the needle;
   introducing a growth medium into the vial through the needle; and
   incubating the vial with the growth medium disposed therein.

* * * * *